United States Patent [19]

Halbert et al.

[11] Patent Number: 4,681,958
[45] Date of Patent: Jul. 21, 1987

[54] DITHIOACID VANADIUM SULFIDE DIMER COMPOSITIONS

[75] Inventors: Thomas R. Halbert, Annandale; Edward I. Stiefel, Bridgewater, both of N.J.

[73] Assignee: Exxon Research and Engineering Company, Florham Park, N.J.

[21] Appl. No.: 787,154

[22] Filed: Oct. 15, 1985

[51] Int. Cl.$^4$ .............................................. C07F 9/00
[52] U.S. Cl. ....................... 556/42; 556/19; 556/25; 556/38
[58] Field of Search ........................ 556/38, 19, 25, 42

[56] References Cited

U.S. PATENT DOCUMENTS

| | | | |
|---|---|---|---|
| 3,297,733 | 1/1967 | Kornicker | 556/38 |
| 3,707,498 | 12/1972 | Milsom | 252/33.6 |
| 3,988,249 | 10/1976 | Gencarelli et al. | 252/33.6 |
| 4,098,705 | 7/1978 | Sakurai et al. | 252/33.6 |
| 4,315,826 | 2/1982 | Schlicht et al. | 556/38 X |
| 4,428,861 | 1/1984 | Bridger | 556/25 X |
| 4,585,882 | 4/1986 | Stiefel et al. | 556/38 |

OTHER PUBLICATIONS

Chemical Abstracts 72 112052m (1970).
Chemical Abstracts 90 132003w (1978).
Chemical Abstracts 83 78839p (1975).
Chemical Abstracts 76 20804n (1971).
Bollinger et al, Organometallics, 1982, I, pp. 1551–1553.
Bollinger et al, J. Am. Chem. Soc., 1983, 105, pp. 6321–6323.
Gambarotta et al, J. Chem. Soc., Chem. Commun., 1983, pp. 184–186.
Larkworthy et al, Inorganica Chemica Acta, 74 (1983), pp. 155–158.
Kuch et al, Organometallics 1983, 2, pp. 350–351.
Szeymies et al, Angew. Chem. Int. Ed. Engl., 23, (1984), 10, pp. 804–805.

*Primary Examiner*—Helen M. S. Sneed
*Attorney, Agent, or Firm*—E. Thomas Wheelock; Joseph J. Dvorak

[57] ABSTRACT

This invention relates to neutral complexes of dithioacid vanadium sulfide dimer and to a method of producing the complexes. The 1,1-dithioacid may be a dithiocarbamate, xanthate, dithiophosphate, dithiophosphinate or other similar ligand. The structure is generally of the form

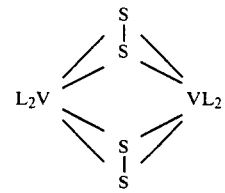

where L is a 1,1-dithioacid. The preferred dithioacid is dithiocarbamate. The compositions are suitable for producing hydrotreating catalysts or as a lubricant additive.

14 Claims, 1 Drawing Figure

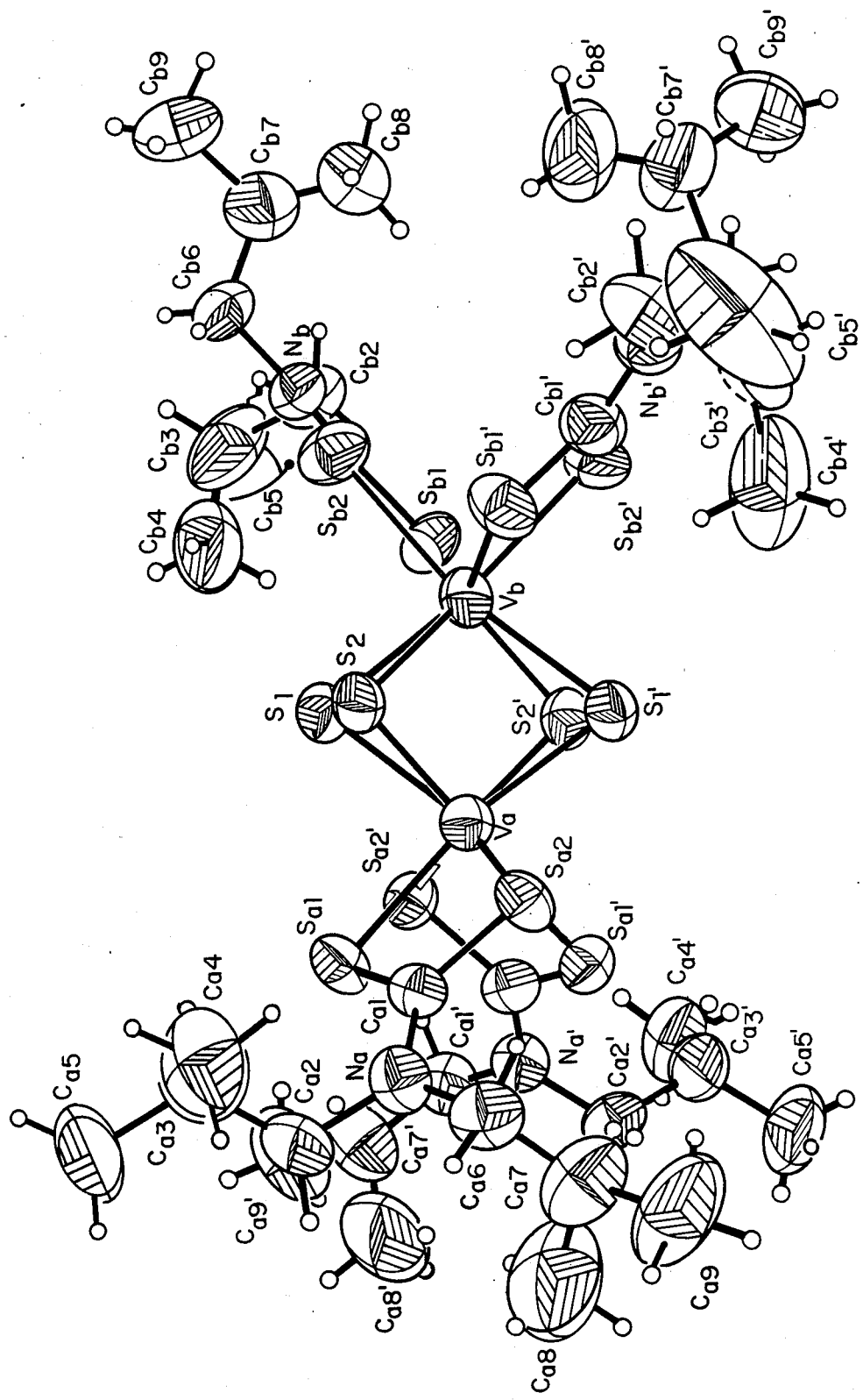

DITHIOACID VANADIUM SULFIDE DIMER COMPOSITIONS

FIELD OF THE INVENTION

This invention relates to neutral vanadium sulfide dimers complexed by dithioacid ligands and to a method of producing the complexes. The 1,1-dithioacid may be a dithiocarbamate, xanthate, dithiophosphate, dithiophosphinate or other similar ligand. The structure is generally of the form

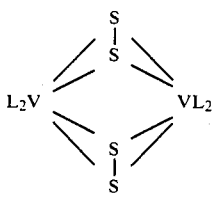

where L is a 1,1-dithioacid. The preferred dithioacid is dithiocarbamate. The compositions are suitable for producing hydrotreating catalysts or as lubricant additives.

BACKGROUND OF THE INVENTION

Various other polynuclear vanadium-sulfur complexes are known. For instance, Szeymies et al, Angew. Chem. Int. Ed. Engl. 22 (1983) No. 11, pp. 885, 886; Dorfman et al, Inorg. Chem. 1983, 22, pp. 3179–3181; and Wiggins et al, J. Chem. Soc., Chem. Commun., 1983, pp. 1313–1315 all disclose the existence of $[V_2(SCH_2CH_2S)_4]^{2-}$. Other vanadium-sulfur complexes containing multiple vanadium atoms are shown in Bollinger et al, Organometallics 1982, I, pp. 1551–1553 (($C_5H_4CH_3$)$_2V_2S_5$) and Bollinger et al, J. Am. Chem. Soc. 1983, 105, pp. 6321–6323 ((i-PrC$_5$H$_4$)$_2$V$_2$S$_4$ and (C$_5$H$_5$)$_2$V$_2$S$_2$(S$_2$C$_2$(CF$_3$)$_2$)).

Single vanadium atom-containing complexes are disclosed in Gambarotta et al, J. Chem. Soc., Chem. Commun., 1983, pp. 184–186; Larkworthy et al, Inorganica Chimica Acta, 74 (1983), pp. 155–158; Kuch et al, Organometallics 1983, 2, pp. 350–351; and Szeymies et al, Angew. Chem. Int. Ed. Engl., 23, (1984), 10, pp. 804–805.

None of these references disclose neutral vanadium sulfide dimers complexed by dithioacid ligands having the structure

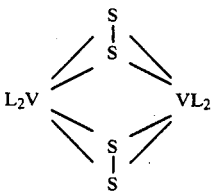

SUMMARY OF THE INVENTION

This invention deals with compositions of matter containing $V_2S_4^{4+}$ cluster cores. The compositions are neutral complexes of 1,1-dithioacids and $V_2S_4^{4+}$ of the general formula L$_2$VS$_4$VL$_2$. The dithioacids amy be xanthates, dithiophosphinates, dithiophosphates, dithiocarbamates, or other similar ligands. The preferred ligand is a dithiocarbamate (S$_2$CNR$_2$) wherein R is independently an H or a C$_1$ to C$_{24}$ linear, branched, or cyclic alkyl group; a C$_6$ to C$_{24}$ aryl, alkaryl, or aralkyl group; or mixtures thereof.

The structures are generally of the form

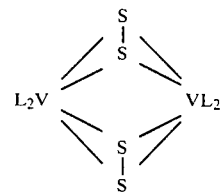

where L is one or more of the dithioacids noted above.

The compositions are useful as catalysts or catalyst precursors for removing sulfur-bearing compounds from sulfur containing hydrocarbon streams. They are also useful as lubricant additives.

The compositions may be made by reacting (NH$_4$)$_3$VS$_4$ with compounds such as substituted thiuramdisulfide in nonaqueous media under an inert atmosphere.

BRIEF DESCRIPTION OF THE DRAWING

The drawing is a depiction of the molecular structure of one species of the invention, tetraisobutyldithiocarbamate vanadium sulfide dimer, determined via x-ray diffraction of a single crystal of the compound.

DESCRIPTION OF THE PREFERRED EMBODIMENTS

The invention encompasses neutral complexes of dithioacid vanadium sulfide dimers having the following general structure:

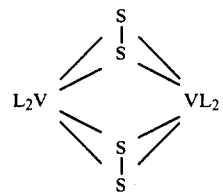

The "L" is a 1,1-dithioacid ligand which may be a dithiocarbamate, xanthate, dithiophosphate, dithiophosphinate or other similar ligand. The preferred ligand is a dithiocarbamate (S$_2$CNR$_2$) wherein R is independently an H or a C$_1$ to C$_{24}$ branched, linear, or cycloalkyl group, e.g., preferably methyl, ethyl, propyl, butyl, isobutyl, t-butyl, or the like; a C$_6$ to C$_{24}$ aryl, alkaryl, or aralkyl group. Each of these groups may be additionally substituted, if so desired, depending upon the final use to which the complex is put. The ligands are preferably all of the same type, however, such is not necessary.

These complexes may be made by reacting (NH$_4$)$_3$VS$_4$ with the oxidized form of the thioacid or thioacids which are to be included in the final inventive complex. For instance, the oxidized form of the dithiocarbamate ligand is the thiuramdisulfide. By way of example, thiuramdisulfides useful for forming the dithiocarbamate form of the complex are of the formula:

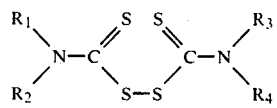

wherein $R_1$, $R_2$, $R_3$ and $R_4$ are the same or different and each may independently be of the type defined for R above.

The reaction should take place in a relatively low polarity solvent which will dissolve the reactants. Dichloromethane, toluene, benzene, etc. are typical of such solvents. Also desirably included in the solvent is at least a small but effective amount of a dipolar aprotic solvent such as dimethylformamide or dimethylsulfoxide. The aprotic solvent is believed to have the function of aiding the dissolution of the difficulty soluble $(NH_4)_3VS_4$ salt.

The mixture may be stirred but such is not necessary. The reaction typically will take place at room temperature and pressure. As noted above, the gas above the reaction phase should be an inert gas such as argon, nitrogen, etc. However, the product of the reaction, once isolated, is typically not air sensitive.

The following is an example of one species and presentation of the example is intended only to demonstrate the invention and not limit it in any way.

EXAMPLE

A sample of tetraisobutylthiuramdisulfide (10.22 gm or 0.025 mole) was dissolved in a solution of 50 ml. $CH_2Cl_2$ containing 1 ml. dimethylformamide under an inert atmosphere. Solid $(NH_4)_3VS_4$ (2.3 gm. or 0.01 mole) was added and the resulting mixture stirred for about 48 hours at room temperature. The mixture was filtered and the solid obtained was extracted with $CH_2Cl_2$ until the washings were almost clear. A dark brown crystalline product was precipitated by the addition of hexane to the combined $CH_2Cl_2$ washes. The $CH_2Cl_2$ was removed under vacuum. After filtration and drying, 6.46 gm. of crude product was obtained. Recrystallization from toluene/hexane yielded 3.1 gm.

The product was submitted for infrared (i.r.) and x-ray diffraction analysis. The i.r. spectral analysis showed absorbances in the region between 600 and 250 cm$^{-1}$; which absorbances are characteristic of briding $S_2^{2-}$ ligands and $R_2NCS_2^-$ ligands bound to vanadium. The characteristic bands for the above product occur at 590 cm$^{-1}$ (medium), 535 cm$^{-1}$ (weak), 440 cm$^{-1}$ (weak), and 378 cm$^{-1}$ (medium).

The single crystal x-ray diffraction analysis was used to produce the molecular depiction shown in the Figure.

The analysis was carried out in the following manner. Large single crystals of the product $V_2S_4(S_2CN(C_4H_9)_2)_4$ were grown by slow evaporation from hexane/$CH_2Cl_2$ solutions of the complex. One crystal was selected and mounted on a computer controlled Nicolet Autodiffractometer equipped with a graphite monochromatized Mo$_\alpha$ ($\lambda=0.71073$ Å) radiation source. The crystal was found to be monoclinic, space group C2/c. Least squares refinement of 15 computer centered reflections ($2\theta > 20°$) at ambient temperature (20°±1° C.) gave the following lattice constants: $a=30.268(6)$ Å, $b=17.481(4)$ Å, $c=17.523(4)$ Å, $\beta=143.38°$. Cell volume was 5530 Å$^3$, $z=4$ and the calculated density 1.258 g/cm$^3$.

A total of 5238 reflections were then collected and the structure of the complex determined from these data following known procedures.

As is illustrated in the Figure, $V_2S_4(S_2CN(C_4H_9)_2)_4$ consists of a pair of V atoms bridged by two $S_2^{2-}$ ligands. Each V atom is further coordinated by two chelating dithiocarbamate ligands, such that each V ends up bonded to 8 S atoms (4 from $S_2^{2-}$ ligands and 4 from dithiocarbamate). The bond lengths around the V atom labelled $V_a$ are set forth in the Table below; bond lengths around $V_b$ are essentially the same. The S—S distance of 1.998 Å reveals the presence of $S_2^{2-}$ ligands in this complex.

TABLE

| Bond | Length, Å |
|---|---|
| $V_a$—$V_b'$ | 2.851(1) |
| $V_a$—$S_1$ (disulfide) | 2.402(2) |
| $V_a$—$S_2$ (disulfide) | 2.403(1) |
| $V_a$—$S_{a1}$ (dtc) | 2.492(1) |
| $V_a$—$S_{a2}$ (dtc) | 2.501(2) |
| S—S (disulfide) | 1.998(2) |

It should be understood that the foregoing disclosure, description and example are only illustrative of the invention. Various changes to the details of the invention would be apparent to the skilled worker and may be made within the scope of the appended claims without departing from the spirit of the invention.

We claim as our invention:

1. Neutral vanadium sulfide dimer complex of the general formula $L_2VS_4VL_2$ wherein L as a 1,1-dithioacid ligand.

2. Neutral vanadium sulfide dimer complex of the general formula $L_2VS_4VL_2$ having the structure:

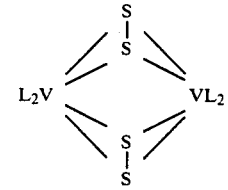

wherein L is a 1,1-dithioacid.

3. The complex of claim 2 wherein the dithioacid is selected from the group consisting of dithiophosphate, dithiophosphinate, xanthate, and dithiocarbamate.

4. The complex of claim 3 wherein the dithioacid is dithiocarbamate of the formula $S_2CNR_2$ and wherein each R independently is H or a substituted or nonsubstituted $C_1$ to $C_{24}$ branched, linear, or cycloalkyl group, or a $C_6$ to $C_{24}$ aryl, alkaryl, aralkyl group.

5. The complex of claim 4 wherein each R is the same.

6. The complex of claim 5 wherein each R is isobutyl.

7. A method for preparing a dithioacid vanadium sulfide dimer complex of the general formula $L_2VS_4VL_2$ wherein L comprises a 1,1-dithioacid ligand, said method comprising the steps of mixing an oxidized dithioacid and $(NH_4)_3VS_4$ in a mixture of a weakly polar solvent and a small but effective amount of a dipolar aprotic solvent for a time sufficient to produce said complex and recovering said complex.

8. The process of claim 7 wherein the dithioacid is selected from dithiophosphate, dithiophosphinate, xanthate, and dithiocarbamate.

9. The process of claim 7 wherein the dithioacid is dithiocarbamate and the oxidized dithioacid is a thiuramdisulfide of the formula:

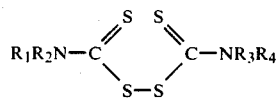

wherein each of $R_1$, $R_2$, $R_3$ and $R_4$ may independently be H or a $C_1$ to $C_{24}$ branched, linear or cycloalkyl group or a $C_6$ to $C_{24}$ aryl, alkaryl or aralkyl group.

10. The process of claim 9 wherein each of $R_1$, $R_2$, $R_3$ and $R_4$ are isobutyl.

11. The complex of claim 1 wherein the dithioacid is selected from the group consisting of dithiophosphate, dithiophosphinate, xanthate, and dithiocarbamate.

12. The compositions of claim 11 wherein the dithioacid is a dithiocarbamate of the formula $S_2CNR_2$ and wherein each R independently is H or a substituted or nonsubstituted $C_1$ to $C_{24}$ branched, linear, or cycloalkyl group, or a $C_6$ to $C_{24}$ aryl, alkaryl or aralkyl group.

13. The complex of claim 12 wherein each R is the same.

14. The complex of claim 13 wherein each R is isobutyl.

* * * * *